United States Patent
Chou et al.

(10) Patent No.: US 7,642,084 B2
(45) Date of Patent: Jan. 5, 2010

(54) ASSAY SYSTEMS, KITS AND METHODS FOR DETECTING MICROORGANISMS

(75) Inventors: George Chin-Sheng Chou, Tainan Hsien (TW); Chang-Yi Huang, Tainan Hsien (TW)

(73) Assignee: AsiaGen Corporation, Tainan County (TW)

( * ) Notice: Subject to any disclaimer, the term of this patent is extended or adjusted under 35 U.S.C. 154(b) by 502 days.

(21) Appl. No.: 11/086,351

(22) Filed: Mar. 23, 2005

(65) Prior Publication Data

US 2005/0170425 A1 Aug. 4, 2005

Related U.S. Application Data

(62) Division of application No. 10/729,980, filed on Dec. 9, 2003, now Pat. No. 7,575,862.

(51) Int. Cl.
*C12M 3/00* (2006.01)
*C12M 1/34* (2006.01)
*C07H 21/04* (2006.01)

(52) U.S. Cl. .............. 435/285.1; 435/283.1; 435/287.2; 435/6; 435/243; 435/501; 435/518; 435/519; 435/526; 536/23.1; 536/23.7; 536/24.3; 536/24.32

(58) Field of Classification Search ............... 435/6, 435/243, 252.1, 253.1, 283.1, 285.1, 287.2; 436/501, 518, 519, 526; 536/23.1, 23.7, 536/24.3, 24.32
See application file for complete search history.

(56) References Cited

U.S. PATENT DOCUMENTS

2001/0019826 A1* 9/2001 Ammann ................. 435/6

* cited by examiner

*Primary Examiner*—Rodney P. Swartz
(74) *Attorney, Agent, or Firm*—WPAT, P.C.; Anthony King; Kay Yang (57) ABSTRACT

The present invention relates to an assay system, kits and methods for detecting microorgansims (especially for *M. tuberculosis*) of a suspected patient. The present invention also relates to an apparatus for performing the integration of thermal and magnetic control in the same apparatus to largely reduce the whole process of *M. tuberculosis* detection to less than 5 hours.

18 Claims, 6 Drawing Sheets

FIG. 6

SEQUENCE LISTING

```
<160> NUMBER OF SEQ ID NOS: 11

<210> SEQ ID NO 1
<211> LENGTH: 280
<212> TYPE: DNA
<213> ORGANISM: Mycobacterium tuberculosis

<400> SEQUENCE: 1
ggccgcggga attcgattgc gtaggcgtcg gtcacaaagg ccacgtaggc gaaccctgcc      60
caggtcgaca cataggtgag gtctgctacc cacagccggt taggtgctgg tggtccgaag     120
cggcgctgga cgagatcggc gggacgggct gtggccggat cagcgatcgt ggtcctgcgg     180
gctttgccgc gggtggtccc ggacaggccg agtttggtca tcagccgttc gacggtgcat     240
ctggccacct cgatgccctc acgaatcact agtgaattcg                           280

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
cgtgagggca tcgaggtggc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
gcgtaggcgt cggtcacaaa                                                  20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
agatgcaccg tcgaacgg                                                    18

<210> SEQ ID NO 5
<211> LENGTH: 19
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 5
gccacgtagg cgaaccctg                                                  19

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Probe

<400> SEQUENCE: 6
tttttttttt acctaaccgg ctgtgggtag caga                                 34

<210> SEQ ID NO 7
<211> LENGTH: 20
<212> TYPE: DNA
<213> ORGANISM: Artificial Sequence
<220> FEATURE:
<223> OTHER INFORMATION: Probe in the MagProbe used in the Examples

<400> SEQUENCE: 7
taaccggctg tgggtagcag                                                 20

<210> SEQ ID NO 8
<211> LENGTH: 18
<212> TYPE: DNA
<213> ORGANISM: Artificial Sequence
<220> FEATURE:
<223> OTHER INFORMATION: Primer No. 4 used in the Examples

<400> SEQUENCE: 8
tgagggcacg aggtggca                                                   18

<210> SEQ ID NO 9
<211> LENGTH: 18
<212> TYPE: DNA
<213> ORGANISM: Artificial Sequence
<220> FEATURE:
<223> OTHER INFORMATION: Primer No. 5 used in the Examples

<400> SEQUENCE: 9
cgtaggcgtc ggtcacaa                                                   18

<210> SEQ ID NO 10
<211> LENGTH: 18
<212> TYPE: DNA
<213> ORGANISM: Artificial Sequence
<220> FEATURE:
<223> OTHER INFORMATION: Primer No. 6 used in the Examples

<400> SEQUENCE: 10
gatgcaccgt cgaacggc                                                   18

<210> SEQ ID NO 11
<211> LENGTH: 17
<212> TYPE: DNA
<213> ORGANISM: Artificial Sequence
<220> FEATURE:
<223> OTHER INFORMATION: Primer No. 7 used in the Examples

<400> SEQUENCE: 11
ccacgtaggc gaaccct                                                    17
```

ASSAY SYSTEMS, KITS AND METHODS FOR DETECTING MICROORGANISMS

CROSS REFERENCE TO RELATED APPLICATIONS

This application is a divisional of U.S. patent application Ser. No. 10/729,980, filed on Dec. 9, 2003, now U.S. Pat. No. 7,575,862, which is hereby incorporated by reference in its entirety for all purposes.

FIELD OF THE INVENTION

The present invention relates to an assay system, kits and methods for detecting microorganisms (especially *M. tuberculosis*) from samples of suspected patient. The present invention also relates to an apparatus that integrates thermal and magnetic control in the same apparatus to largely reduce the hybridization time.

BACKGROUND OF THE INVENTION

*Tuberculosis* (TB) is the leading infectious killer of youth and adults and the first most common infectious disease worldwide. One third of the world's population is currently infected and 20 million of those infected are active cases; TB will kill 30 million people this decade. More than 50 million people may already be infected with multidrug-resistant (MDR) strains of TB. Drug resistance has been brought about because of complacency in the public health sector and poorly managed TB control programs. Prior to MDR *tuberculosis*, the success rate of drug combination treatment was greater than 90%, even in AIDS patients. MDR *tuberculosis*, however, is not only highly infectious but also essentially incurable with a mortality of 50%. TB is now becoming the leading cause of death among HIV positive people where it kills much more rapidly with a fatality of 80%.

*Tuberculosis* is caused by infection with *Mycobacterium tuberculosis*, a bacillus bacterium. It is spread by aerosol droplets and causes irreversible lung destruction. If it escapes the lung it may cause systemic disease affecting many organs including bones, joints, liver, spleen, gastrointestinal tract and brain. 50% of people exposed to *M. tuberculosis* are infected with the bacteria and 15% of those infected develop disease. Poverty, malnutrition and overpopulation contribute dramatically to the perseverance and wild spread of *tuberculosis*.

Past means of controlling TB have involved the use of combinations of antibiotics. Recently, because of complications due to multidrug-resistant strains, the number and combination of antibiotics administered must be individually tailored depending on the strain the patient is harboring. In extreme cases, surgical removal of the infected portion of the lung is required.

Traditionally, the diagnosis of TB has been made on the basis of clinical findings and chest radiographs and confirmed by sputum or tissue smears that show TB bacilli. These methods remain the "gold standard" for diagnosis, but development of DNA probes, polymerase chain reaction (PCR) assays, and liquid media now allow more sensitive and rapid diagnosis. Unfortunately, increased sensitivity of rapid techniques is not always associated with increased specificity.

Skin testing should be used in conjunction with other clinical findings and is not a sensitive or specific test for establishing the diagnosis when the patient had been vaccinated with BCG or infected by *Mycobacterium* other than *tuberculosis*. In extrapulmonary TB, site-specific tissue or fluid samples or both are submitted for smear, culture, and histological analysis. Typically, histological features of a tuberculous lesion include caseating and noncaseating granulomata with giant cells. Rapid laboratory testing to identify and determine the drug susceptibility of *M. tuberculosis* isolates is vital to effective diagnosis, treatment, and control of TB in the community.

Clearly, expedient diagnosis is important in controlling the spread of *tuberculosis*. Sputum samples, evaluated first by direct microscopic evaluation (smear), are visualized with either the easily detected acid-fast fluorochrome dye auramine O, or the more specific Ziehl-Neelsen stain. Specimens are cultured on either solid media (Lowenstein-Jensen slant), or are grown in a liquid medium, such as the BACTEC automated radiometric system. Next, biochemical or nucleic acid probe testing is used to identify various strains. Isolates are tested for resistance to commonly used antituberculosis drugs, often by using the new method of susceptibility testing in liquid broth rather than the traditional agar dilution method.

The Ziehl-Neelsen carbolfuchsin or Kinyoun carbolfuchsin stains have been essential in TB diagnosis for nearly 100 years. Although less sensitive than culture, the acid-fast smear is a rapid and inexpensive test that can be performed with a minimum of equipment and is very specific for mycobacteria. Depending on the bacterial load, a single sputum smear has sensitivity between 22% and 80%, but the yield is improved when multiple sputum specimens are examined.

Most laboratories in the United States use fluorochrome stains, such as auramine-rhodamine stain. With these techniques, mycobacteria fluoresce with a bright orange color and can be easily seen on low-power microscopy, increasing the sensitivity of the smears.

The Amplified *Mycobacterium Tuberculosis* Direct Test (Gen-Probe) targets mycobacterial ribosomal RNA by transcription-mediated amplification. The test uses DNA probes that are highly specific for M *M. tuberculosis* species. It is best used (and only approved for use) in patients in whom acid-fast bacilli smears are positive and cultures are in process. Since specificity is less than 100%, even in patients with positive smears, occasional false-positive results do occur, usually in patients with nontuberculous mycobacterial infections.

This technique amplifies even very small portions of a predetermined 20 target region of *M. tuberculosis*-complex DNA. The test uses an automated system that can rapidly detect as few as one organism from sputum, bronchoalveolar lavage, blood, cerebrospinal fluid, pleural fluid, or other fluid and tissue samples and has shown sensitivity and specificity of nearly 90% in pulmonary disease.

The Mantoux test is the preferred and standard skin test for detecting TB. It involves injection of 5 TU of purified protein derivative (PPD, tuberculin), usually 0.1 mL, intradermally. Induration is then assessed at 48 to 72 hours. The extent of induration (not erythema) should be measured across two diameters at right angles and the two measurements then averaged. Interobserver variability can be decreased through the use of a ballpoint pen carefully brought from outside the zone of induration toward the center. As the area of induration is reached, resistance increases, and marking should stop at the outer edge of induration. However, about 20% of patients with active TB may have negative skin tests, and some populations have an even higher incidence of false-negative results. For example, false-negative rates up to 50% have been reported in patients with advanced HIV infection. Alternately, false-positive results may occur in patients infected by other nontuberculous mycobacteria (e.g., *Mycobacterium*

*avium* complex). Therefore, a negative skin test never rules out TB, and a positive skin test alone does not establish the diagnosis.

The U.S. Centers for Disease Control and Prevention and the World Health Organization recommend initial susceptibility testing for all *M. tuberculosis* isolates because of the emergence of drug resistance worldwide.

This ingenious assay uses the fluorescent capabilities of fireflies genetically implanted in *M tuberculosis*. The procedure offers the possibility of testing mycobacterial drug susceptibility in hours. It is in the development stages but may become widely available in the next few years.

Given the above, current available assays cannot quickly and completely detect *M. tuberculosis*. It requires a quick assay with high specificity and sensitivity detect *M. tuberculosis* from available samples.

SUMMARY OF THE INVENTION

The present invention relates to an assay system, kits and methods for detecting microorganisms (especially *M. tuberculosis*) from the samples of suspected patient.

The present invention also relates to an apparatus for performing the dissociation of nucleic acid double strands, hybridization, washing, the separation of magnetic beads and thermal control in the same apparatus.

BRIEF DESCRIPTION OF THE DRAWINGS

FIG. 1 shows the outline of the detection method of the invention.

FIG. 2 shows *M. tuberculosis* genomic DNA detected by the kit of the invention.

FIG. 3 shows the identification of *M. tuberculosis* by the assay of the invention.

FIG. 4 shows the specificity of the assay of the invention.

FIG. 5 shows the specificity and sensitivity of the kit of the invention.

FIG. 6 shows the apparatus of the invention.

DETAILED DESCRIPTION OF THE INVENTION

The present invention provides a method for detecting microorganism DNA comprising:

(a) hybridizing the microorganism cDNA with microorganism-specific probes in hybridization tubes wherein each probe is linked to magnetic bead;
(b) transferring hybridization tubes to magnetic wells for washing;
(c) adding blocking solution into the tubes;
(d) adding avidin enzyme complex or streptavidin enzyme complex into the tubes;
(e) performing washing reaction to remove interfering material by the aid of magnetic field;
(f) suspending magnetic beads; and
(g) detecting the luminescent or color change after adding substrate of enzyme.

The method of the present invention can be applied in any microorganisms including virus, bacteria, fungi etc. The method of the present invention is particularly suitable for detecting *Mycobacterium tuberculosis.*

In general, any body fluid such as CSF, serum, blood, sputum, pleural effusion, throat swab and stools can be used in the clinical tests. The preferred samples for *M. tuberculosis* are from CSF, serum, blood, sputum, pleural effusion, and throat swab.

Polymerase Chain Reaction (PCR) PCR is described in Saiki et al. (1985), *Science,* 230 1350. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target DNA can be amplified a million fold or more in about two to four hours. PCR is a molecular biology tool which must be used in conjunction with a detection technique to determine the results of amplification. In the present invention, biotinylated primer pairs are used in the PCR amplification.

As used herein, a "probe" is a substance, e.g., a molecule, that can be specifically recognized by a particular target. Generally, probes will be linked to solid support to facilitate the separation of DNA. In the invention, the probes linked to magnetic beads (MagProbe) are preferred. The sequence of the probe in MagProbe is amine-TAACCGGCTGTGGGTAGCAG.

Commonly employed labels include, but are not limited to, biotin, fluorescent molecules, radioactive molecules, chromogenic substrates, chemi-luminescence, and the like. The methods for biotinylating nucleic acids are well known in the art, as are methods for introducing fluorescent molecules and radioactive molecules into oligonucleotides and nucleotides.

When biotin is employed, it is detected by avidin, streptavidin or the like, which is conjugated to a detectable marker, such as an enzyme (e.g., horseradish peroxidase). Enzyme conjugates are commercially available from, for example, Vector Laboratories (Burlingame, Calif.). Steptavidin binds with high affinity to biotin, unbound streptavidin is washed away, and the presence of horseradish peroxidase enzyme is then detected using a luminescence-emission substrate in the presence of peroxide and appropriate buffers. The product may be detected using a Berthold Luminometer (Pforzheim, Germany).

Detection methods are well known for fluorescent, radioactive, chemiluminescent, chromogenic labels, as well as other commonly used labels. Briefly, chemiluminescence can be identified and quantitated most directly by their emission wavelengths and intensity.

To achieve the integration of thermal and magnetic control in one device facilitating the operation, the present invention also provides an apparatus for performing the dissociation of nucleic acid double strands, hybridization, washing, the separation of magnetic beads and thermal control in the same apparatus, comprising:

(a) the means for fitting reaction containers;
(b) the means for controlling the temperature of the containers; and
(c) the means for controlling the magnetic force of the containers, wherein the means for controlling the temperature of the containers are connected to the means for fitting reaction containers, and the means for controlling the magnetic force of the containers are connected to the means for fitting reaction containers.

In particular, the means for controlling the temperature of the containers heats the containers to perform the dissociation of nucleic acid double strands according to temperature change. The thermal controllers are easily bought from the device market. Because most of operating procedure after hybridization involves MagProbe, the means for controlling the magnetic force of the containers are integrated with the thermal controller to make the apparatus of the invention. In particular, the means for controlling the magnetic force of the containers perform the magnetic change of magnetic bead to facilitate hybridization washing and the separation of magnetic beads in the containers.

The present invention also provides a diagnostic kit for detecting microorganism cDNA comprising:

(a) a probe linked to magnetic bead;
(b) bioactive primers;
(c) avidin enzyme complex or streptavidin enzyme complex; and
(d) enzyme substrate.

In the kit, the bioactive primers are made by reacting DNA labeling reagent with the primers. The DNA labeling reagent is one reagent labeling DNA. While not limiting the scope of the present invention, the preferred reagent is the compound having the formula:

Fu-BE-D wherein Fu represents a furocoumarin derivative selected from the group consisting of angelicin derivatives and psoralen derivatives; wherein BE represents none or a binding enhancer selected from the group consisting of C4-12 alkyl, alkyenyl, polyalkylamine and polyethylene glycol; and wherein D represents a detectable group selected from the group consisting of: biotin, fluorescence, acridinium ester and acridinium-9-carboxamide. The most preferred DNA labeling reagent is 9-(4-aminomethyl-4,5'-dimethylangelicin) acridinium carboxamide.

An assay system for detecting microorganisms, the system comprising:

(i) diagnostic kit for detecting microorganism cDNA comprising:
  (a) a probe linked to a magnetic bead;
  (b) bioactive primers;
  (c) avidin enzyme complex or streptavidin enzyme complex; and
  (d) enzyme substrate
(ii) an apparatus for performing the dissociation of nucleic acid double strands, hybridization, washing, the separation of magnetic beads and thermal control in the same apparatus, comprising:
  (a) the means for fitting reaction containers;
  (b) the means for controlling the temperature of the containers; and
  (c) the means for controlling the magnetic force of the containers, wherein the means for controlling the temperature of the containers are connected to the means for fitting reaction containers, and the means for controlling the magnetic force of the containers are connected to the means for fitting reaction containers;

(iii) a magnetic rack to bind the magnetic bead on the wall of the containers; and
(iv) a detector.

In the assay system of the invention, the kit further comprises hybridization buffer, washing buffer and blocking buffer. These buffers are easily purchased from commercial suppliers such as Pierce, Biolab, Qiagen etc. In general, the assay system of the invention can reduce the whole process of *M. tuberculosis* detection to less than 5 hours.

EXAMPLES

The examples below are non-limiting and are merely representative of various aspects and features of the present invention.

Material and Methods
Major Kit I:
(1) Lysis Buffer 1 (5 ml)
(2) Lysis Buffer II (4 ml)
(3) Hybridization Buffer (5 ml)
(4) Wash Buffer (60 ml)
(5) Lysis tubes (1.8 ml, 25 tubes)
(6) Hybridization tubes (12×75 mm, 50 tubes)
(7) Extension buffer (3 ml, stored in −20° C. after arriving)
Major Kit-II: (50 reactions/kit, store in 4° C.)
(1) MagProbe (450 µl, stored in 4° C. after arriving)
Detection kit-I: (250 reactions/kit, store in 4° C.)
(1) Blocking buffer (0.5%, 60 ml, stored in 4° C.)
(2) Substrate A (7.5 ml, stored in 4° C.)
(3) Substrate B (7.5 ml, stored in 4° C.)
Detection kit-II: (250 reactions/kit, store in −20° C.)
(1) Bioactive catalyst (BC; 1 mg/ml, 15 µl, stored in −20° C.)
Other material and equipments:
(1) Magnetic Rack
(2) NALC (N-acetyl-L-cysteine)
(3) 4% NaOH solution
(4) 2.94% sodium citrate solution
(5) PBS, pH7.0
(6) 0.1% PBST.(PBS with 0.1% tween-20)
(7) 0.5% PBST (PBS with 0.5% tween-20)
(8) Magnetic Dry Bath
(9) Berthol Luminometer with PC connection
Procedures:
I. Decontamination of Clinical Samples (performed in P3 level laboratory by each medical center)
(1) Collect and keep clinical samples in 4° C. refrigerator.
(2) Dissolve 1 g of NALC into 100 ml of sterile 4% NaOH and 100 ml of 2.94% sodium citrate solution (Daily prepared).
(3) Add equal volume of NaOH-citrate-NALC into each clinical sample.
(4) Vortex for 30 second and invert sample tube for several times. Keep in room temperature (RT) for 15 minutes.
(5) Add PBS to 50 ml level of sample tube, then centrifuge at 3000 rpm for 20 minutes.
(6) Remove supernatant and use 1 ml of PBS to resuspend precipitate.
II. Lysis of Precipitate (can be performed in P2 laboratory)
(1) Mix 10 ml ddH$_2$O with 1 ml of resuspended precipitate. Vortex 20 sec, then. centrifuge at 3,800 rpm for 15 min.
(2) Remove supernatant; add 150 µl of Lysis buffer I and vortex for 1 min. Keep at RT for 10 min.
(3) Keep Lysis tube in 100° C. water bath for 20 min and then add 125 µl of Lysis buffer II.
(4) Centrifuge at 10,000 rpm for 2 min, collect DNA lysate and store it in −20° C. freezer.
III. Target amplification: two steps Step 1:
(1) Set up a new 0.2 ml microfuge tube by adding the following reagent:

| Reagent | Volume |
| --- | --- |
| DNA | 1 µl |
| Reaction mixture* | 49 µl |

-continued

| Reagent | Volume |
|---|---|
| *The reaction mixture contains the following cocktail: | |
| 10× extension buffer | 5 μl |
| #4 primer(TGAGGGCACGAGGTGGCA) | 5 μl |
| #5 primer(CGTAGGCGTCGGTCACAA) | 5 μl |
| dNTP | 1 μl |
| Taq DNA polymerase (2 U/μl) | 0.5 μl |
| ddH$_2$O | 32.5 μl |

1. Initiate the following program with heated lid enabled Extension program:

| | Temperature | Time | Number of cycles |
|---|---|---|---|
| 1 | 94° C. | 5 min | 1 cycle |
| 2 | 94° C. | 30 sec | 30 cycles |
| | 62.5° C. | 15 sec | |
| | 72° C. | 15 sec | |
| 3 | 72° C. | 10 min | 1 cycle |
| 4 | 4° C. | Hold | — |

Step II:
1. Set up a new 0.2 ml microfuge tube by adding up the following:

| Reagent | Volume |
|---|---|
| PCR product from step I | 15 μl |
| Reaction mixture* | 35 μl |
| *The reaction mixture contains the following cocktail: | |
| 10× extension buffer | 5 μl |
| #6 primer(GATGCACCGTCGAACGGC) | 5 μl |
| #7 primer(CCACGTAGGCGAACCCT) | 5 μl |
| dNTP | 1 μl |
| Taq DNA polymerase (2 U/μl) | 0.5 μl |
| ddH$_2$O | 18.5 μl |

2. Initiate the extension program.

*Extension program is the same as step I.

IV. Hybridization (1) In a hybridization tube, mix 125 μl of ddH2O, 15 μl of MagProbe, 150 μl of hybridization buffer and 10 μl of each amplified DNA sample together.
(2) Keep hybridization tubes at 100° C. dry bath for 5 min.
(3) Transfer hybridization tubes to a 60° C. dry bath and hold for 20 min.
(4) Transfer hybridization tubes to magnetic wells of a magnetic dry bath and hold for 5 min.
(5) Remove hybridization buffer by aspiration.
(6) Add 1 ml of pre-heated 60° C. wash buffer to each tube, vortex and put tubes back in magnetic wells and hold for 5 min.
(7) Remove hybridization buffer by aspiration.
(8) Repeat Steps 6-7.
(9) Keep hybridization tubes at RT.

V. Detection (1) Add 200 μl of blocking solution into each tube, vortex.
(2) Add 5 μl of freshly prepared BC (99 μl 0.1% PBST+1 μl BC stock), vortex and disperse evenly. Sit at RT for 20 min. Avoid light.
(3) Put hybridization tubes into magnetic rack and sit for 5 min. Then remove solution by aspiration.
(4) Add 1 ml of 0.5% PBST, vortex and put tubes back to magnetic rack. Sit for 5 min then remove solution by aspiration. Repeat once.
(5) Use 200 μl of PBS each tube to resuspend magnetic beads by vortexing.
(6) Take 20 μl of resuspend solution from step 5.
(7) Add 50 μl of mixed substrate to each tube (25 μl substrate A+25 μl substrate B).
(8) Read luminescence by Luminometer.

VI. Interpretation of Results (1) ≧100,000 RLU :Positive for *M. tb* complex
(2) <25,000 RLU :Negative for *M. tb* complex
(3) 25,000~100,000 RLU : Probable *M. tb* complex positive; Retest to verify results.
(4) Retest value ≧25,000 RLU: Positive for *M. tb* complex.
(5) Retest value <25,000 RLU: Negative for *M. tb* complex.

Example 1

Figure 1:
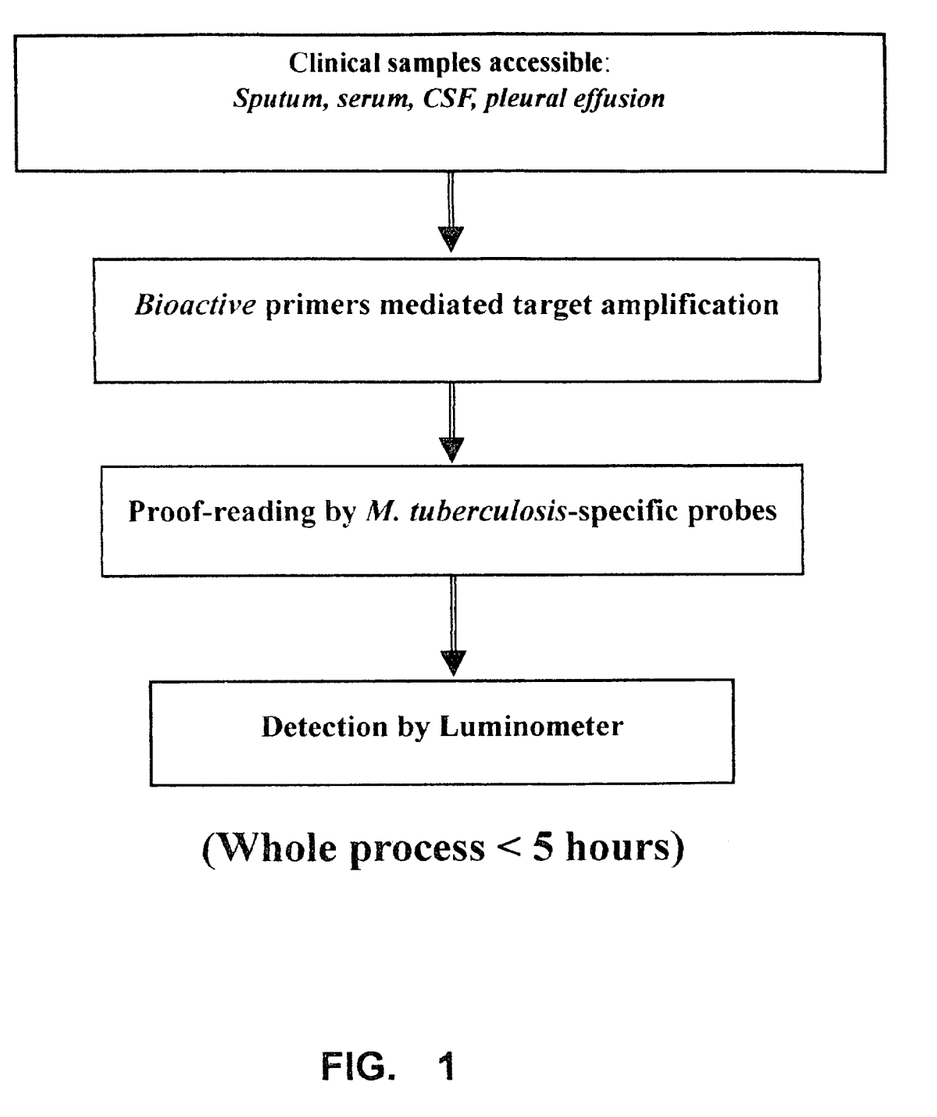
Figure 2:
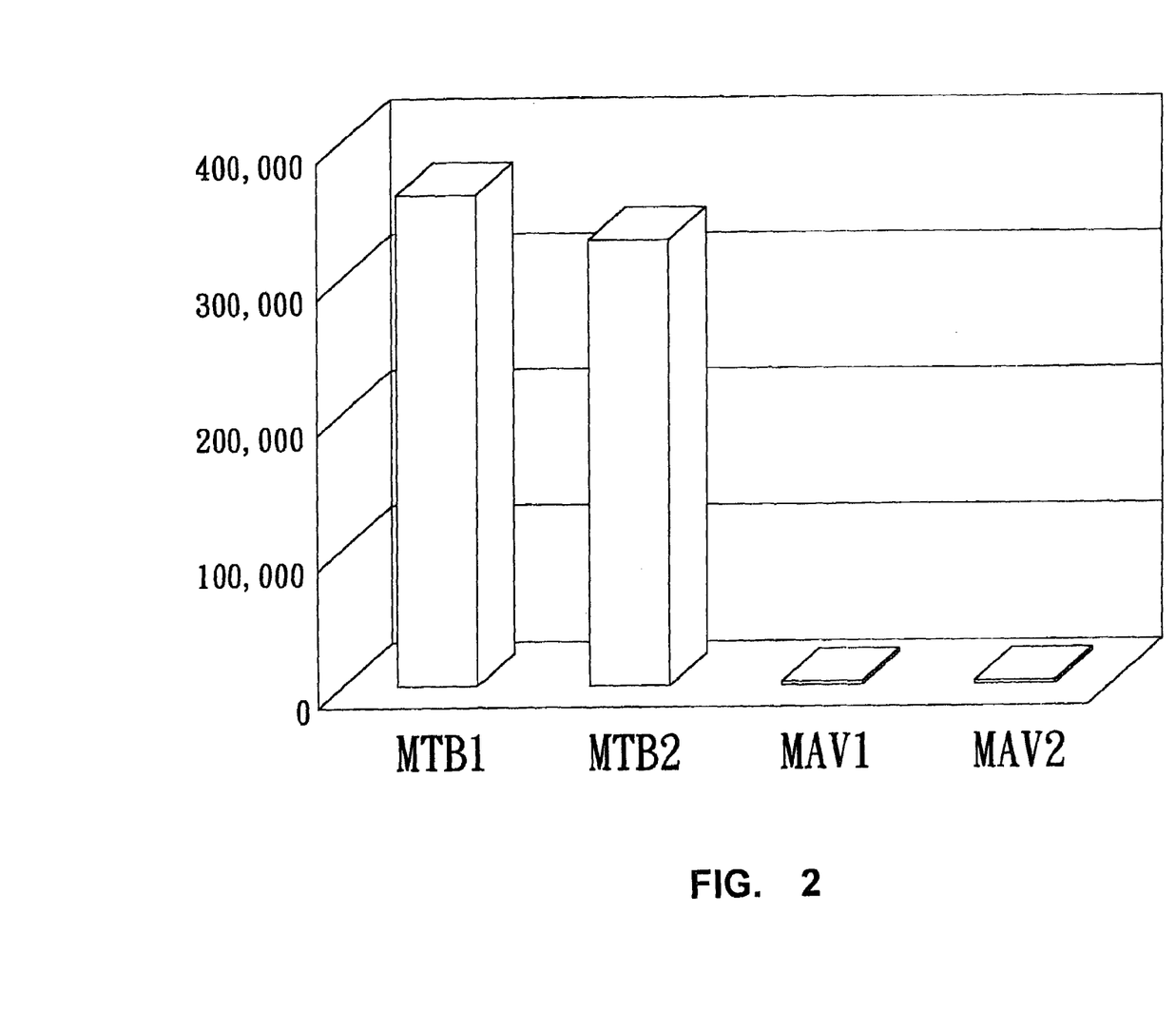

Following the above procedures, ten fentogram (10 fg) of mycobacterial genomic DNA from both *M. tb* and *M. avium* were analyzed. It is clearly indicated in FIG. 2 that *M. tb* could be differentiated from *M. avium*, suggesting that this detection kit could detect as low as 1 to 20 copies of *M. tb*.

Example 2

Figure 3:
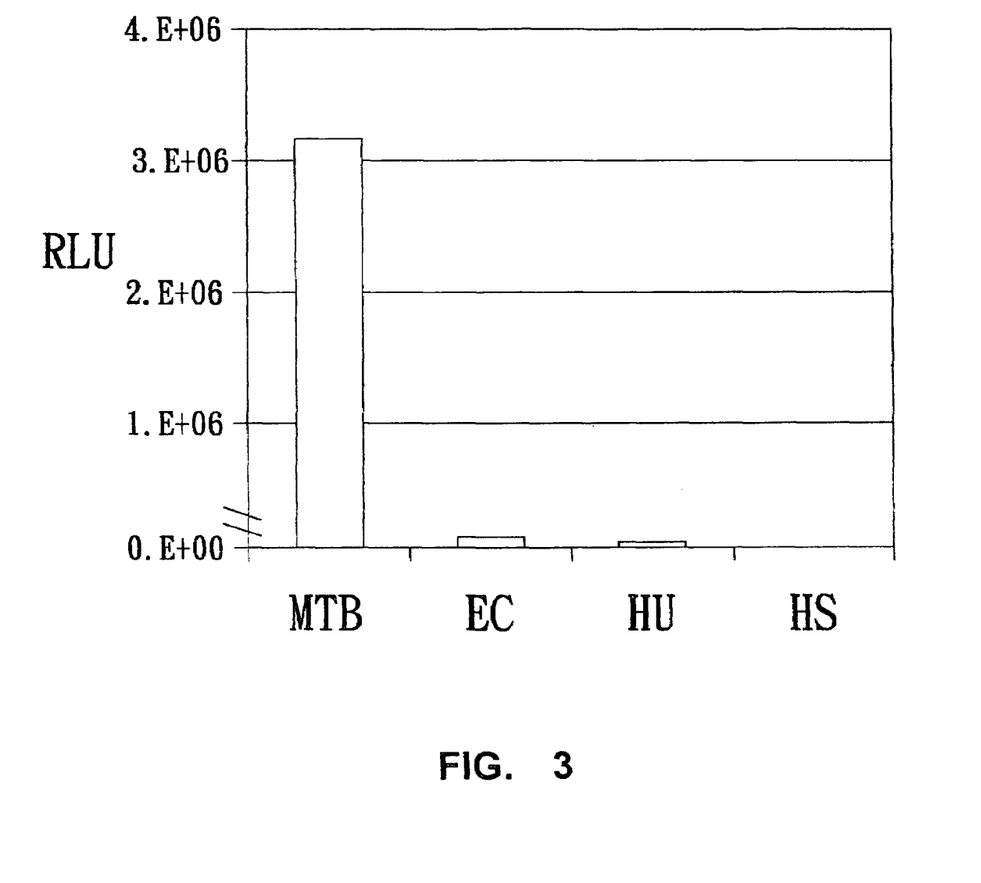

As indicated in FIG. 3, MTB assay specifically detected. *M. tuberculosis* (MTB) in contrast to *E. coli* (EC), human DNA (HU) or Herring Sperm DNA (HS).

Example 3

Figure 4:
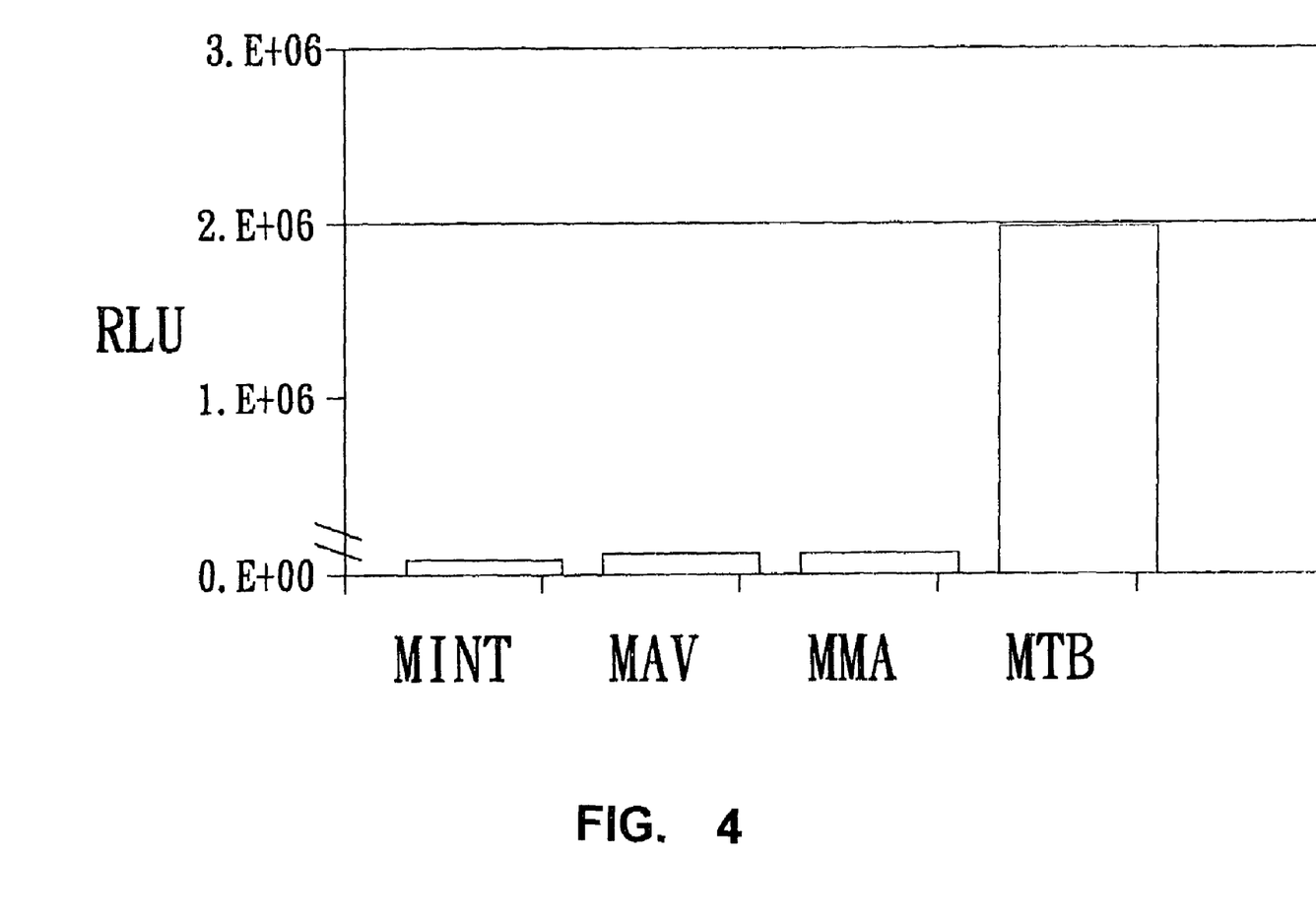

Different samples were assayed by the assay system of the invention. It is clearly shown in FIG. 4 that MTB assay specifically detected *M. tuberculosis* but not MOTT (*Mycobacterium* Other Than *Tuberculosis*) including *M. marinum* (Mma), *M. avium* (Mav) and *M. intracellulare* (Mint) from clinical samples.

Example 4

Figure 5:
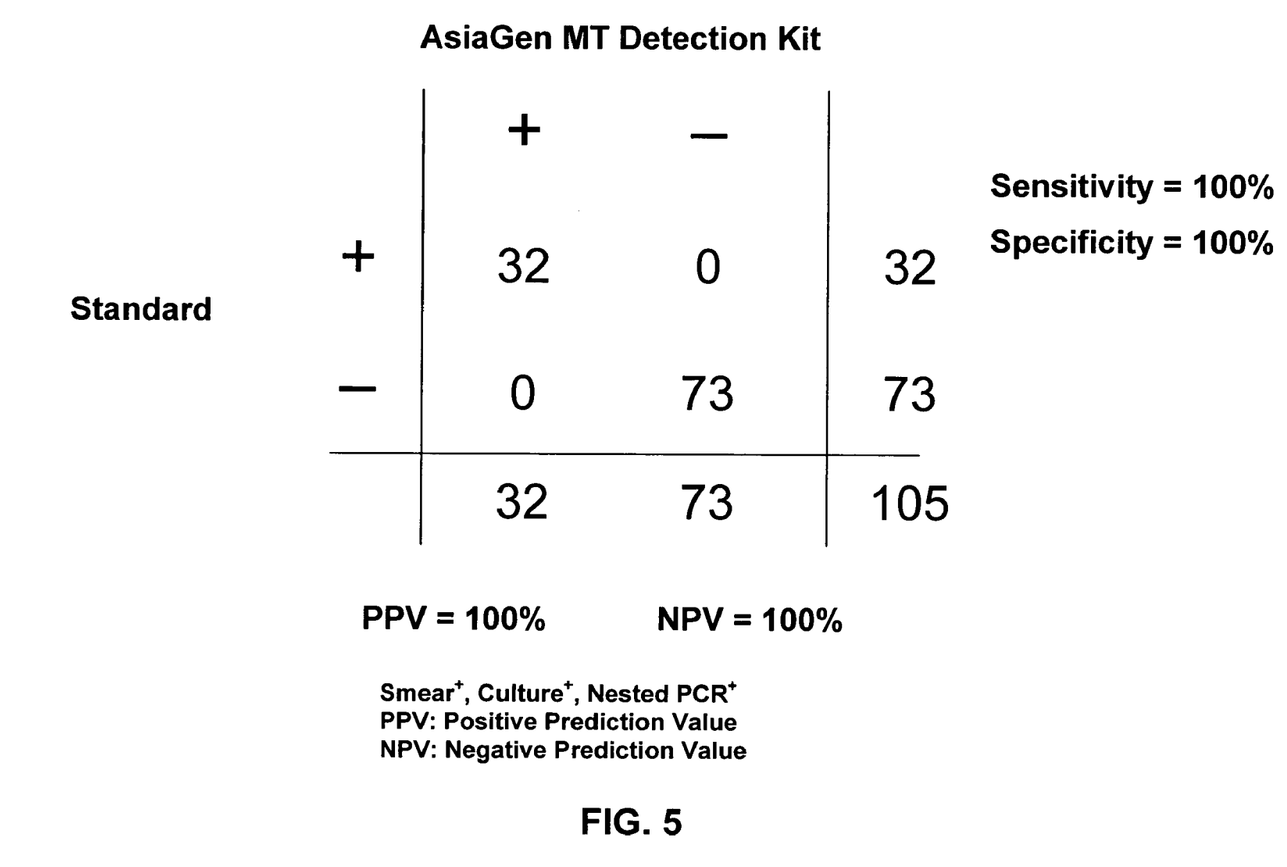
Figure 6:
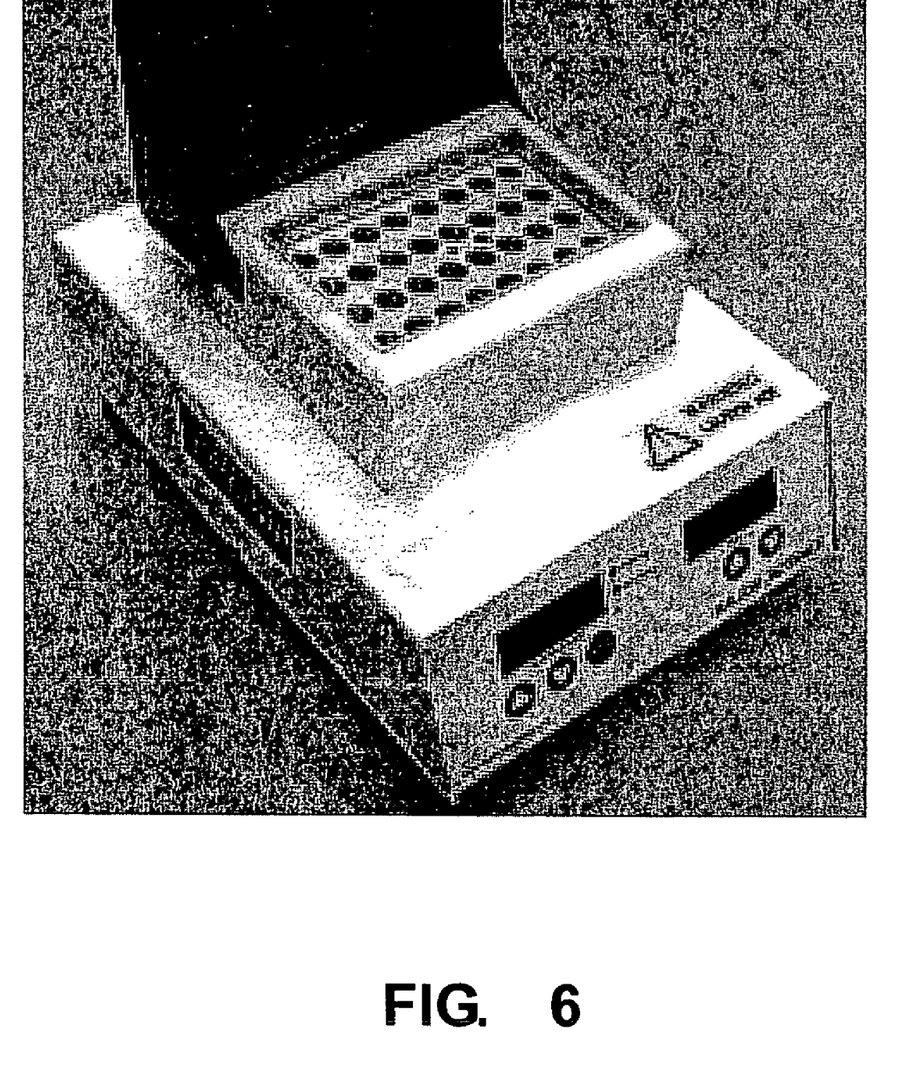

Clinical samples, both positive and negative cases determined by smear test, culture confirmation and Nested-PCR, were examined by the invention. The results in FIG. 5 were identical to that mentioned prior. These results had shown that the *M. tuberculosis* detection kits of the invention achieved extremely high sensitivity and specificity.

While the invention has been described and exemplified in sufficient detail for those skilled in this art to produce and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that various substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. An apparatus for performing denaturation of double-stranded nucleic acids, hybridization, washing, separation of magnetic beads and thermal control in the same apparatus, comprising:
   (a) a means for fitting reaction containers arranged in multiple rows;
   (b) a means for providing the thermal control to the reaction containers; and
   (c) a means for providing a magnetic force to the reaction containers,
   wherein the means for providing the thermal control is in connection with the means for fitting reaction containers, and the means for providing the magnetic force and the means for fitting reaction containers are integrated in the apparatus.

2. The apparatus of claim 1, wherein the means for providing the thermal control to the reaction containers heats the containers to perform the denaturation of the double-stranded nucleic acids.

3. The apparatus of claim 1, wherein the means for providing the magnetic force are integrated in the apparatus at the location outside the top and bottom rows of the reaction containers.

4. The apparatus of claim 1, wherein the means for providing the magnetic force cause the magnetic beads to bind onto walls of the reaction containers at the top and bottom rows.

5. The apparatus of claim 1, wherein the means for providing the magnetic force exert no magnetic force to the reaction containers at the inner rows and thereby magnetic beads are not bound onto the walls of the containers therein.

6. An assay system for detecting a microorganism comprising:
   (i) a diagnostic kit for detecting DNA of the microorganism comprising:
      (a) a probe attached to magnetic beads;
      (b) bioactive primers;
      (c) an avidin enzyme complex or streptavidin enzyme complex; and
      (d) an enzyme substrate;
   (ii) an apparatus for performing denaturation of double-stranded nucleic acids, hybridization, washing, separation of magnetic beads and thermal control in the same apparatus, comprising:
      (a) a means for fitting reaction containers arranged in multiple rows;
      (b) a means for providing the thermal control to the reaction containers; and
      (c) a means for providing a magnetic force to the reaction containers,
      wherein the means for providing the thermal control is in connection with the means for fitting reaction containers, and the means for providing the magnetic force and the means for fitting reaction containers are integrated in the apparatus; and
   (iii) a detector capable of detecting a color change, wherein the probe comprises a nucleotide sequence specific for, and is capable of hybridizing with, the DNA of the microorganism.

7. The assay system of claim 6, wherein the bioactive primers are capable of amplifying genomic DNA of *M. tuberculosis*.

8. The assay system of claim 6, wherein the streptavidin enzyme complex is streptavidin horseradish peroxidase (SA-HRP).

9. The assay system of claim 6, wherein the probe comprises a nucleotide sequence set forth by amine-TAACCG-GCTGTGGGTAGCAG (SEQ ID NO. 7).

10. The assay system of claim 6, wherein the detector is a luminometer or a spectrophotometer.

11. The assay system of claim 7, wherein at least one of the primers is labeled by a DNA labeling reagent.

12. The assay system of claim 7, wherein the primers comprise:
   a. an outer pair of primers comprising nucleotide sequences set forth by TGAGGGCACGAGGTGGCA (SEQ ID NO: 8) and CGTAGGCGTCGGTCACAA (SEQ ID NO: 9), respectively;
   b. an inner pair of primers comprising nucleotide sequences set forth by GATGCACCGTCGAACGGC (SEQ ID NO: 10) and CCACGTAGGCGAACCCT (SEQ ID NO: 1), respectively.

13. The assay system of claim 12, wherein at least one of the inner pair of the primers is conjugated with biotin.

14. The assay system of claim 12, wherein the inner pair of primers are conjugated with biotin.

15. The assay system of claim 11, wherein the DNA labeling reagent is aminomethyl-4,5'-dimethylangelicin acridinium carboxamide.

16. The assay system of claim 6, wherein the means for providing the magnetic force are integrated in the apparatus at the location outside the top and bottom rows of the reaction containers.

17. The assay system of claim 6, wherein the means for providing the magnetic force cause the magnetic beads to bind onto walls of the reaction containers at the top and bottom rows.

18. The assay system of claim 6, wherein the means for providing the magnetic force exert no magnetic force to the reaction containers at the inner rows and thereby magnetic beads are not bound onto the walls of the containers therein.

* * * * *